US00PP35483P2

(12) United States Plant Patent
Danziger

(10) Patent No.: US PP35,483 P2
(45) Date of Patent: Nov. 14, 2023

(54) ***LIMONIUM* PLANT NAMED 'DANLIMECNT'**

(50) Latin Name: *Limonium perezii*
Varietal Denomination: DANLIMECNT

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 18/109,478

(22) Filed: Feb. 14, 2023

(51) Int. Cl.
*A01H 5/02* (2018.01)
*A01H 6/00* (2018.01)

(52) U.S. Cl.
USPC ..... Plt./358; Plt./449
CPC ..... *A01H 6/00* (2018.05)

(58) Field of Classification Search
USPC ..... Plt./358, 449
CPC ..... A01H 5/02
See application file for complete search history.

(56) References Cited

PUBLICATIONS

CPVO Register—CPVO Application Consultation Version 4.8.16 for *Limonium* 'DANLIMECNT'; Jun. 3, 2023; 3 pages.*

* cited by examiner

*Primary Examiner* — Kent L Bell
(74) *Attorney, Agent, or Firm* — Cassandra Bright

(57) ABSTRACT

A new and distinct cultivar of *Limonium* plant named 'DANLIMECNT' is disclosed, characterized by abundant, brilliant purple flowers and reduced fragility. The new variety is a *Limonium*, typically produced as an ornamental plant.

2 Drawing Sheets

Figure 1:
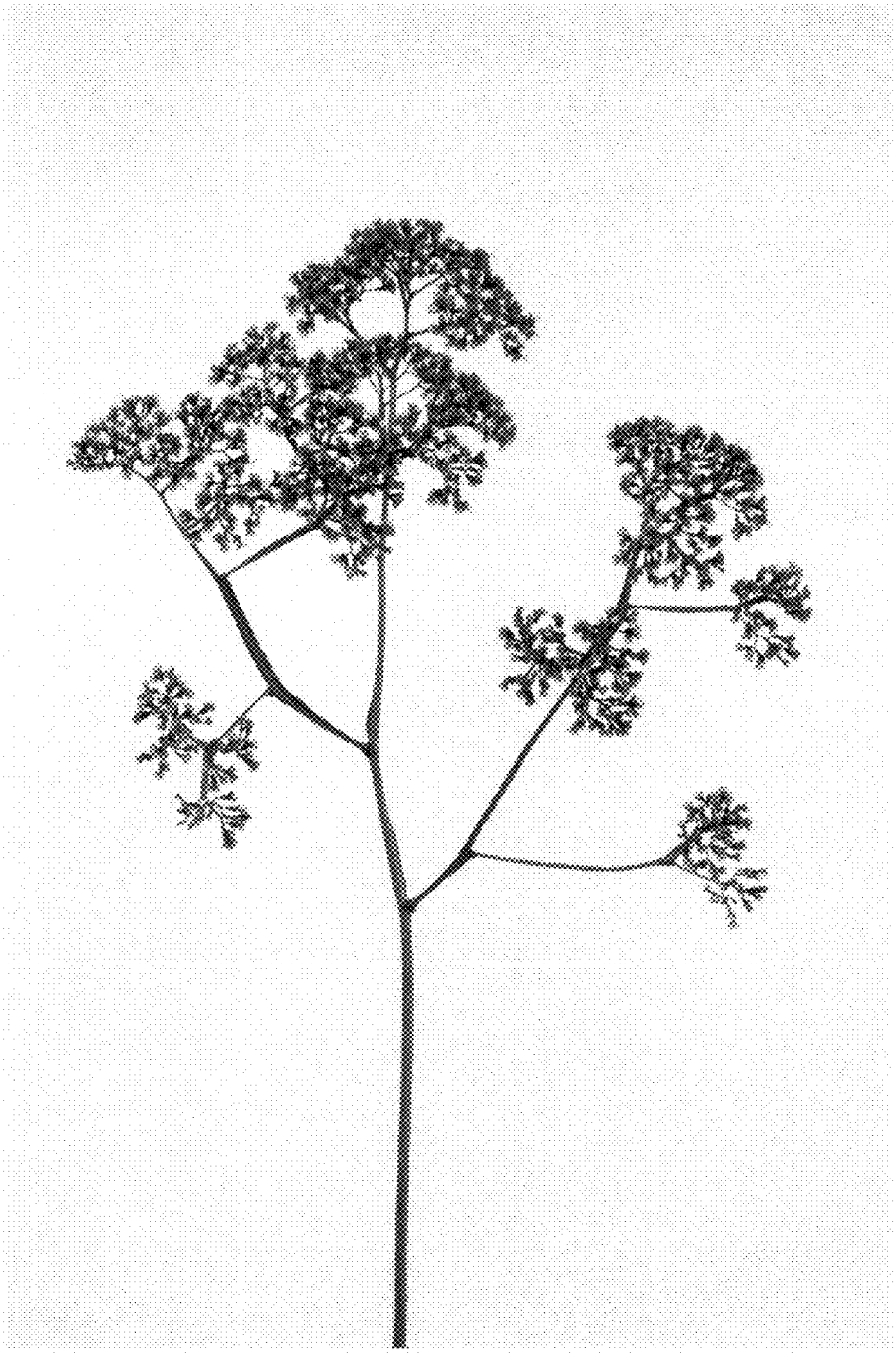

Latin name of the genus and species: *Limonium perezii.*
Variety denomination: 'DANLIMECNT'.

BACKGROUND OF THE INVENTION

The new *Limonium* cultivar is a product of a planned breeding program conducted by the inventor, Gavriel Danziger in Moshav Mishmar Hashiva, Israel. The objective of the breeding program was to produce new *Limonium* varieties for ornamental horticultural production. The open-pollination resulting in this new variety was made during spring of 2016.

The seed parent is the unpatented, propriety variety referred to as *Limonium* 'LPE-15-25'. The pollen parent is unknown. The new variety was discovered in spring of 2017 by the inventor in a group of seedlings resulting from the 2016 open-pollination, in a greenhouse in Moshav Mishmar Hashiva, Israel.

Asexual propagation of *Limonium* 'DANLIMECNT' was performed by tissue culture in May of 2018, at a research laboratory in Moshav Mishmar Hashiva, Israel. Subsequent asexual propagation has shown that the unique features of this cultivar are stable and reproduced true to type in successive generations. Extensive confidential testing has been performed to determine and define the desirable characteristics of the new variety.

Date of first sale is Feb. 20, 2022, in Kenya. This sale was made directly by the inventor or one who obtained the claimed invention directly or indirectly from the inventor. This sale and all public disclosures made between Feb. 20, 2022, and the filing of this application fall within the exception allowed under 102(b)(1).

SUMMARY OF THE INVENTION

The cultivar 'DANLIMECNT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANLIMECNT'. These characteristics in combination distinguish 'DANLIMECNT' as a new and distinct *Limonium* cultivar:

1. Abundant flowering.
2. Brilliant purple flower color.
3. Reduced fragility; stronger stems.

PARENT COMPARISON

Plants of 'DANLIMECNT' are similar in some horticultural characteristics to the seed parent. The new variety, however, differs in the following:

1. Flowers of the new variety are darker in color than flowers of the seed parent.
2. Plants of the new variety are less fragile than plants of the seed parent.
3. Flower stems of the new variety are longer than flower stems of the seed parent.

COMMERCIAL COMPARISONS

Plants of 'DANLIMECNT' are similar in some horticultural characteristics to the variety *Limonium* 'Safora Oshi Pink', unpatented. The new variety, however, differs in the following:

1. Flowers of the new variety are purple, while flowers of this comparator are pink.

2. Inflorescences of the new variety are shaped as is typical of the *perezii* species, clumping and nearly rounded; inflorescences of this comparator are more open and flattened.
3. Leaves of the new variety are ovate shaped, while leaves of this comparator are pinnately lobed.

Plants of 'DANLIMECNT' are similar in some horticultural characteristics to the variety *Limonium* 'Safora Blue Tiful', unpatented. The new variety, however, differs in the following:

1. Flowers of the new variety are darker in color than flowers of this comparator.
2. Inflorescences of the new variety are shaped as is typical of the *perezii* species, clumping and nearly rounded; inflorescences of this comparator are more open and flattened.
3. Leaves of the new variety are ovate shaped, while leaves of this comparator are pinnately lobed.

BRIEF DESCRIPTION OF THE PHOTOGRAPHS

The accompanying photograph in FIG. 1 illustrates in full color a typical inflorescence of 'DANLIMECNT' harvested from a plant at about 9 months of age, grown in the ground.

Figure 2:
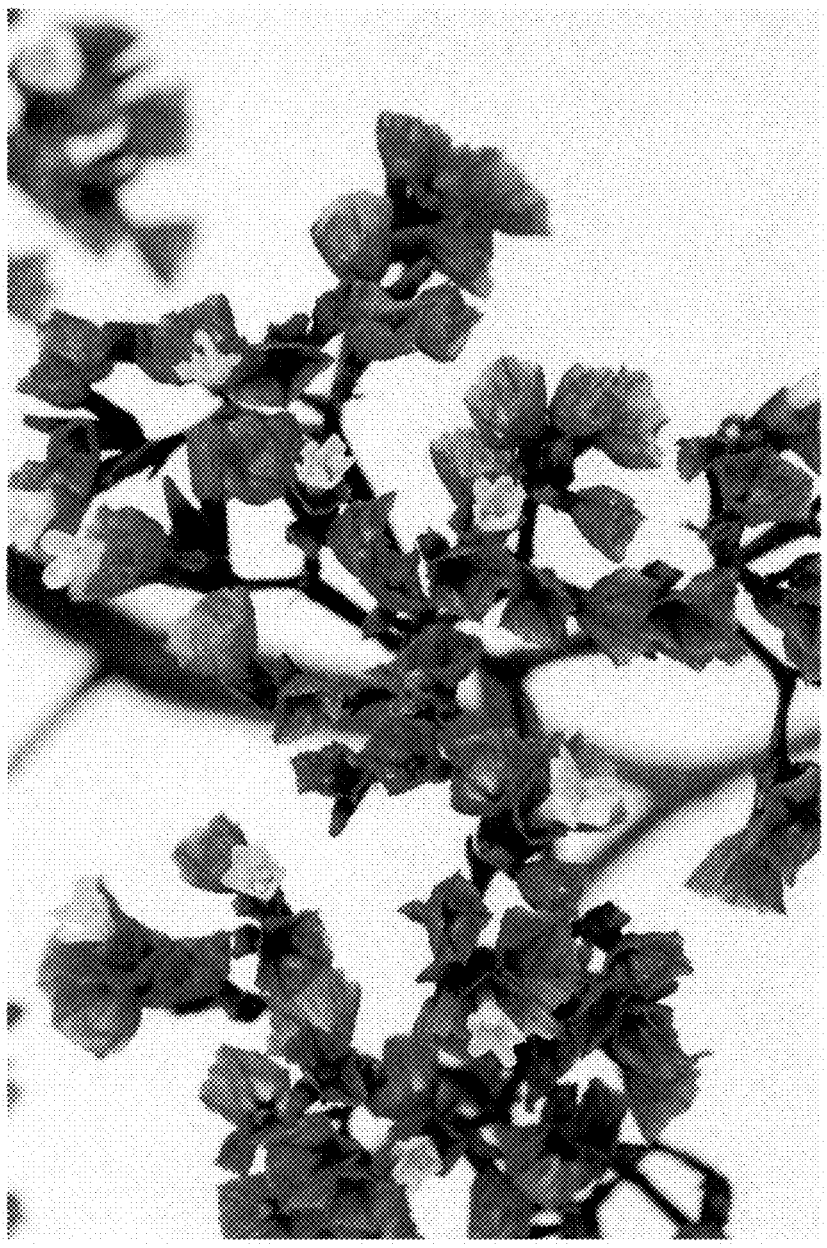

FIG. 2 illustrates a close-up view of typical flowers of the new variety. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANLIMECNT' plants grown in a greenhouse in Moshav Mishmar Hashiva, Israel, under natural lighting. Measurements were taken during Autumn. The growing temperature ranged from approximately 18° C. to 27° C. during the days, 10° C. to 15° C. during the nights. Measurements and numerical values represent averages of typical plant types.

Botanical classification: *Limonium perezii* 'DANLIMECNT'.

PROPAGATION

Time to initiate rooting: Comes with roots while they are in tissue culture. Approximately 10 to 15 days to produce more roots in plugs, with temperature range of 10° C.-30° C.

Age of plant described: Approximately 9 months.

Root description: Woody, strong. Colored RHS Olive-Gray 197B.

PLANT

Plant type: Perennial.

Height: Approximately 15 cm to top of foliar plane. Approximately 70 cm to top of floral plane.

Plant spread: Approximately 40 cm.

Growth rate: Moderately vigorous.

Branching characteristics: Non-branching.

FOLIAGE

Leaf:

*Arrangement.*—Basal rosette.
*Quantity.*—Approximately 60 to 100.
*Average length.*—27 cm.
*Average width.*—8 cm.
*Shape.*—Ovate.
*Apex.*—Obtuse.
*Base.*—Rounded.
*Margin.*—Entire.
*Texture.*—Top Surface: Smooth and powdery. Bottom Surface: Smooth.
*Aspect.*—Outward.
*Color.*—Young Foliage, Upper Side: Near RHS Green 137B. Young Foliage, Under Side: Near RHS Green 137B. Mature Foliage, Upper Side: Near RHS Yellow-Green 146B. Mature Foliage, Under Side: Near RHS Green 138B.
*Venation.*—Type: Linear. Color, Upper Side: Near RHS Green 138A. Color, Under Side: Near RHS Yellow-Green 148C.

Petiole:

*Length.*—Approximately 13 cm.
*Diameter.*—Approximately 0.6 cm.
*Color.*—Near RHS Green 137C.
*Texture.*—Smooth.

FLOWER

Natural flowering season: Summer to autumn.

Flower stems per plant: Average range 8 to 9.

Inflorescence and flower type and habit: Erect, stable, compound corymb with wings on pedicel.

Rate of flower opening: Approximately 7 days.

Longevity as cut flower: 10 to 15 days.

Flowers per inflorescence: 125.

Average inflorescences per plant: 8 to 9.

Inflorescence size:

*Height.*—Approximately 8 cm.
*Width.*—Approximately 5 cm.

Individual flowers:

*Length.*—Approximately 0.7 cm.
*Width.*—Approximately 0.5 cm.
*Shape.*—Tubular, partially fused.

Bud:

*Shape.*—Oblong.
*Length.*—Approximately 0.5 cm.
*Diameter.*—Approximately 0.1 cm.
*Color.*—Near RHS Violet N88B.

Petals:

*Quantity.*—5 in a single whorl.
*Arrangement.*—Rotate.
*Shape.*—Oblong.
*Length.*—Approximately 0.5 cm.
*Width.*—Approximately 0.4 cm.
*Texture.*—Smooth.
*Margin.*—Entire.
*Apex.*—Retuse.
*Base.*—Cuneate.
*Appearance.*—Matte.
*Color.*—When Opening: Upper Surface: Near RHS White 155A. Lower Surface: Near RHS White 155A. Fully Opened: Upper Surface: Near RHS White 155A. Lower Surface: Near RHS White 155A.

Sepals:

*Quantity.*—5.

*Arrangement.*—Fused, calyx cup-shaped.

*Length.*—Approximately 0.7 cm.

*Diameter.*—Approximately 0.5 cm.

*Shape.*—Semi-tubular.

*Margin.*—Entire.

*Texture.*—Smooth.

*Apex.*—Truncate.

*Base.*—Cuneate.

*Appearance.*—Matte.

*Color.*—Fully Opened: Upper Surface: Near RHS Violet N87C. Lower Surface: Near RHS Violet 90C.

Peduncle:

*Length.*—Approximately 1.9 cm.

*Width.*—Approximately 0.4-cm.

*Texture.*—Slightly pubescent.

*Angle.*—Approximately 40° to 80°.

*Strength.*—Strong.

*Color.*—Near RHS Yellow-Green 143A.

Pedicels/secondary peduncles:

*Length.*—Approximately 0.3 cm.

*Width.*—Approximately 0.2 cm.

*Texture.*—Smooth.

*Aspect.*—Outward.

*Strength.*—Strong.

*Color.*—Near RHS Yellow-Green 143A.

Fragrance: Absent or weak.

REPRODUCTIVE ORGANS

Androecium:

*Stamens.*—Quantity: 5. Filament Length: Approximately 0.7 cm. Filament Color: Near RHS White 155B.

*Anthers.*—Shape: Elliptical. Length: About 0.1 cm. Color: RHS Yellow 9C. Pollen: Color: Near RHS Green-Yellow 1C. Amount: Abundant.

Gynoecium:

*Pistil.*—Quantity: 5 per flower. Length: Approximately 0.4 cm. Style Color: Near RHS White 155D. Stigma: Shape: Capitate. Color: Near RHS White 155D. Ovary Color: Near RHS White 155D.

OTHER CHARACTERISTICS

Seeds and fruits: One single seed per flower, stiff and black, closest to RHS 202A. About 0.1 cm in size.

Disease/pest resistance: Typical resistance and susceptibility to diseases and pests common to *Limonium.*

Temperature tolerance: Tolerates temperatures from 10° C. to 35° C.

What is claimed is:

1. A new and distinct cultivar of *Limonium* plant named 'DANLIMECNT' as herein illustrated and described.

* * * * *